United States Patent
Maeda et al.

(10) Patent No.: US 6,520,311 B1
(45) Date of Patent: Feb. 18, 2003

(54) MULTI-ROW TYPE ONLINE INTERNAL QUALITY INSPECTION DEVICE

(76) Inventors: Hiromu Maeda, 1-17, Uchinodai 1-chome, Hamakita-shi, Shizuoka 434-0045 (JP); Kazuo Haraguchi, 2406-4, Ichinocho, Hamamatsu-shi, Shizuoka 435-0051 (JP)

(*) Notice: Subject to any disclaimer, the term of this patent is extended or adjusted under 35 U.S.C. 154(b) by 0 days.

(21) Appl. No.: 09/916,542

(22) Filed: Jul. 27, 2001

(51) Int. Cl.[7] .............................................. B65G 29/00

(52) U.S. Cl. .................... 198/339.1; 198/458; 209/588; 209/912

(58) Field of Search .............................. 198/339.1, 458; 414/222.01; 250/223; 209/576, 577, 588, 587, 912, 938, 939

(56) References Cited

U.S. PATENT DOCUMENTS

| | | | | |
|---|---|---|---|---|
| 2,488,230 A | * | 11/1949 | Page ........................... | 198/30 |
| 3,147,844 A | * | 9/1964 | Mountz ....................... | 198/34 |
| 3,148,761 A | * | 9/1964 | Niederer et al. ............ | 198/33 |
| 3,379,299 A | * | 4/1968 | Griner ......................... | 198/30 |
| 3,389,776 A | * | 6/1968 | Carvallo ..................... | 198/30 |
| 3,662,871 A | * | 5/1972 | Koepnick ................... | 198/30 |
| 3,767,027 A | * | 10/1973 | Pund et al. ................. | 198/32 |
| 3,809,207 A | * | 5/1974 | Euverard ..................... | 198/34 |
| 3,990,572 A | * | 11/1976 | Fishback ..................... | 198/458 |
| 4,129,207 A | * | 12/1978 | Cupp .......................... | 198/445 |
| 4,164,277 A | * | 8/1979 | Fluck et al. ................. | 198/369 |
| 4,281,933 A | | 8/1981 | Houston et al. ............. | 356/425 |
| 4,342,321 A | * | 8/1982 | Zullo .......................... | 131/282 |
| 4,625,856 A | * | 12/1986 | Haas, Sr. et al. ........... | 198/457 |
| 4,800,704 A | * | 1/1989 | Ishii et al. ................... | 53/145 |
| 4,834,605 A | * | 5/1989 | Jerred ..................... | 414/791.7 |
| 4,840,265 A | * | 6/1989 | Sato et al. .................. | 198/446 |
| 4,844,234 A | * | 7/1989 | Born et al. ................. | 198/458 |
| 4,860,882 A | * | 8/1989 | Maeda et al. .............. | 198/458 |
| 4,895,245 A | * | 1/1990 | Bauers et al. ............... | 198/458 |
| 4,913,170 A | * | 4/1990 | Conti .......................... | 131/282 |

(List continued on next page.)

FOREIGN PATENT DOCUMENTS

| | | |
|---|---|---|
| JP | 64-51177 | 2/1989 |
| WO | WO 96/13340 | 5/1996 |
| WO | WO 01/22062 | 3/2001 |

*Primary Examiner*—Christopher P. Ellis
*Assistant Examiner*—Rashmi Sharma
(74) *Attorney, Agent, or Firm*—Reed Smith LLP

(57) ABSTRACT

A multi-row type internal quality inspection device is arranged to adjust spacing intervals between the columns of receiving trays arranged in rows on a conveyer to the column spacing intervals of a supply conveyor at the start part on the entrance side of a transport path; to have the spacing intervals between the receiving trays become wider at an inspection area provided at an intermediate part of the transport path to allow light projecting means and light receiving means to be arranged there in the lateral direction with respect to inspection objects on the receiving trays for adequate inspection of internal quality of the objects through transmission light obtained through them; and, at the end point on the exit side of the transport path, to have the spacing intervals narrowed and adjusted to the column spacing internals of a conveyor of a next process of sorting on the exit side of the transport path. The receiving trays are arranged to be laterally movable on mounting bars which are mounted on conveyor chains in parallel and spaced at a predetermined distance. Guide pins protruding downward from the receiving trays and guide rails disposed below the path of the receiving trays are arranged to gradually widen and narrow the column spacing intervals between the objects. At the inspection area, therefore, the internal quality of the objects can be adequately inspected by light projecting means and light receiving means.

8 Claims, 11 Drawing Sheets

U.S. PATENT DOCUMENTS

| | | | | |
|---|---|---|---|---|
| 4,932,514 A | * | 6/1990 | Doppenberg | 198/445 |
| 4,936,072 A | * | 6/1990 | Creed et al. | 53/282 |
| 4,938,339 A | * | 7/1990 | Benson | 198/458 |
| 5,080,551 A | * | 1/1992 | Jerred | 414/791.7 |
| 5,161,929 A | * | 11/1992 | Lichti, Sr. et al. | 414/331 |
| 5,366,066 A | * | 11/1994 | Boot | 198/458 |
| 5,390,779 A | * | 2/1995 | Spatafora | 198/458 |
| 5,396,980 A | * | 3/1995 | Sobrero | 198/433 |
| 5,935,285 A | * | 8/1999 | Lucas | 65/29.12 |
| 6,012,344 A | * | 1/2000 | Halbo | 73/865.8 |
| 6,116,404 A | * | 9/2000 | Heuft et al. | 198/339.1 |
| 6,193,046 B1 | * | 2/2001 | Segawa et al. | 198/339.1 |
| 6,260,425 B1 | * | 7/2001 | Eder | 73/865.8 |

* cited by examiner

MULTI-ROW TYPE ONLINE INTERNAL QUALITY INSPECTION DEVICE

BACKGROUND OF THE INVENTION

1. Field of the Invention

This invention relates to a multi-row type online internal quality inspection device for non-destructively examining and measuring the inside of objects, such as agricultural products, which are transported and placed one by one on numerous receiving trays arranged in many rows and columns on an endless chain conveyor, by projecting light rays from many lamps on them and by detecting a reflection light which is diffused and reflected from the inside of each of the agricultural products, or a light transmitted through the inside of the product, and by inspecting the internal quality on the basis of the light information thus obtained.

The objects applicable to the internal quality inspection by the above-stated device include, for example, fishery products, such as pearl oysters and fish, and meat of stock farming, etc. However, the following description of this invention is given, by way of example, in connection with the internal inspection of an agricultural product.

2. Description of Related Art

Means for measuring the internal quality of objects such as agricultural products (hereinafter will be referred to as inspection objects) using light rays has been variously contrived to operate by different methods. Such different methods include a reflection light method whereby information on the internal quality is detected through a reflection light obtained from the inspection object by projecting thereon light rays which include near infrared rays, as disclosed, for example, in Japanese Laid-Open Patent Application No. HEI 6-30068; and a transmission light method whereby the internal quality information is detected from a transmission light obtained through the inspection objects by projecting a light on the objects, as disclosed, for example, in Japanese Laid-Open Patent Application No. HEI 7-229840).

These methods relate to detecting and measuring means which consists of transport means for conveying the inspection objects as well as light projecting and light receiving devices for detecting the internal quality information. However, the disclosure made in each of the Japanese laid-open patent applications merely shows the transport means as a single strip of simple transport conveyor arranged to convey inspection objects in a row.

The inventors of the present patent application, therefore, have developed transport means suited for an internal quality inspection device including receiving trays for sorting and screening and an agricultural product screening (and sorting) device. The transport means and the screening device were disclosed in Japanese Patent Publication No. 2891973 and has been put into commercial practice.

The inventors further developed a device arranged to be capable of efficiently obtaining information on the internal quality of inspection objects, irrespective of their sizes, inspection items and kinds, by projecting light over a wide range of the inspection objects with the quantity of light to be projected on the inspection objects increased. This device were disclosed in Japanese Patent Applications No. HEI 11-173916 and No. HEI 11-271151.

In order to inspect the inspection objects in large quantity at sorting and packaging facilities, the above-stated device must be installed in a large number. However, the arrangement of light-projecting and light-receiving means of the device necessitates a transport path to be arranged to increase the dimension of each row of a plurality of receiving trays in the transverse or lateral direction of the transport path. Then, since the spacing intervals between the rows and columns cannot be decreased, the transport (conveyor) path requires a larger installation space, which necessitates some expansion of an existing building of the facilities.

Conventional screening and sorting devices are generally arranged to select and sort or classify the inspection products by grades by detecting and measuring the appearance grade, size and weight of them without any device for detecting internal quality information. The devices of this kind are popularly arranged, at many sorting and packaging facilities, to use a multi-row type sorting conveyor having object receiving trays laterally arranged in each row, for example, as disclosed in Japanese Patent Publication No. SHO 46-26805. The sorting conveyor of this type is generally installed in combination with an automatic supply device which is arranged at a starting part of the conveyor to automatically supply, for example, agricultural products coming from a preceding process. Therefore, the conventional sorting conveyor is suited for processing the products in large quantity. However, the rows of receiving trays on the conveyor are narrowly spaced from each other. Therefore, it has been impossible to arrange, in combination with the conveyor, any light-projecting and receiving means that is arranged to project the rays of light on the agricultural products on each of the receiving trays over a wide range of the peripheral part of each of the agricultural products.

BRIEF SUMMARY OF THE INVENTION

This invention is directed to solve the problems of the prior art described above. It is therefore an object of this invention to provide a multi-row type online internal quality inspection device to be interposed in between an existing automatic supply device arranged to supply inspection objects after a preceding process and an existing conveyor for a subsequent process of screening and sorting the inspection objects by measuring and checking them by their appearance or external quality, such as weight, shape, size or the degree of color, for example, at sorting and packaging facilities. The internal quality inspection device to be provided according to this invention for inspecting the internal quality of the inspection object is aimed to economically arrange it to carry out the interposed internal quality inspection process by utilizing the existing automatic supply device and the existing conveyor for the subsequent process in combination as they are.

More specifically, the multi-row type online internal quality inspection device according to this invention comprises transport means having a transport starting part in which a plurality of transport columns of inspection objects are arranged to coincide in position with the inspection object supply columns of an existing automatic supply device and a transport ending part in which the transport columns are arranged to coincide in position with the inspection object sending columns of the existing conveyor for a subsequent process; and an inspection area comprises light projecting means for projecting light rays on each of inspection objects and light receiving means for receiving and detecting a transmission light coming through the inspection objects. The inspection area is interposed in between the transport starting part and the transport ending part. In the inspecting area, the light ray is projected on each of adjacently arranged inspection objects without having any interference of one object with another, so that the internal quality of each of the inspection objects can be accurately examined and inspected by the multi-row type online internal quality inspection device according to this invention.

The multi-row type online internal quality inspection device according to the present invention comprises:

transport means for conveying a plurality of inspection objects in a plurality of rows, said transport means including an inspection area;

light projecting means arranged at predetermined positions in said inspection area to project light rays on the inspection objects set side by side in each of said rows and conveyed by said transport means;

light receiving means arranged at said inspection area to receive transmission light coming through said inspection objects, wherein said transport means comprises a conveyor having left and right conveyor chains endlessly arranged to circularly travel in parallel on left and right sides of said transport means along chain rails;

a plurality of mounting bars arranged in parallel with each other and a spaced at a predetermined interval in the direction of travel of said conveyor, two ends of each of said mounting bars being held by said conveyor chains on the left and right sides of said transport means;

a plurality of receiving trays carried by said mounting bars to be shiftable by said mounting bars in parallel with said mounting bars and arranged in a plurality of columns spaced in the direction of width of said conveyor and in a plurality of rows arranged in the direction of travel of said conveyor, and a plurality of guide rails arranged to guide said receiving trays so as to vary a spacing interval between adjacent columns of receiving trays in the direction of width of said conveyor.

A first embodiment of the part invention comprises: transport means for conveying many inspection objects in a plurality of rows and also in a plurality columns; an inspection area arranged, at a predetermined intermediate part of the transport path of the transport means, to include light projecting means for projecting light rays on the inspection objects in each of the rows conveyed by the transport means and light receiving means for receiving transmission light coming through the inspection objects. In the multi-row type online internal quality inspection device, the transport means includes a conveyor having left and right conveyor chains endlessly arranged to circularly travel in parallel along chain rails which are arranged in parallel with each other on the left and right sides of the transport means; many mounting bars which are arranged in parallel with each other and spaced at predetermined intervals in the direction of travel of the conveyor; many receiving trays mounted on the mounting bars, to be movable in parallel with the mounting bars, and arranged in a plurality of rows extending in the direction of width of the conveyor and in a plurality of columns in the direction of travel of the conveyor, the receiving trays being respectively arranged to have guide pins protruding downward; and a plurality of guide rails which are arranged to guide the guide pins of the receiving trays to move the receiving trays of each row in parallel with the mounting bars in such a way as to cause the receiving trays of each row to be closer to each other by narrowing spacing intervals between the adjacent (columns of) receiving trays at a transport starting part of the conveyor, to gradually make the receiving tray spacing intervals wider according as each row of the receiving trays is brought closer to the inspection area from the transport start part by the travel of the conveyor and to cause the receiving tray spacing intervals to become narrower and to be equal to the spacing intervals of a conveyor arranged for a subsequent process.

In another aspect of this invention, a multi-row type online internal quality inspection device is arranged as a second embodiment of this invention as follow: In addition to what is described above as the first embodiment of this invention, each of the receiving trays is provided with a loose fitting part which is formed at a lower front part of the tray in the direction of travel of the conveyor and is loosely fitted on the mounting bar located in front of the loose fitting part. Further, each receiving tray is provided also with an inserting cutout part which is formed in the rear side face of the receiving tray and is arranged to be engaging the mounting bar located in rear of the receiving tray. The provision of the loose fitting part and the inserting cutout part effectively keeps each of the receiving trays in a horizontal attitude while the conveyor is horizontally traveling.

Further, in a further aspect of the invention, a multi-row type internal quality inspection device is arranged as a third embodiment of this invention, as follows: In addition to what is described above as the first or second embodiment of this invention, each of the receiving trays is provided with an elastic receiving seat which is fitted into the receiving tray and has a through hole vertically formed in the center part thereof as a transmission light passage; and also with a light blocking bottom face which is arranged on the bottom side of the tray to horizontally extend both frontward and rearward from the hole. The light receiving means thus can be arranged to be closer to the lower side face of each of the receiving trays.

The first embodiment of this invention mentioned above is arranged as follows: The many mounting bars are arranged in front and in rear of each of the plurality of rows of receiving trays in the traveling direction of the conveyor chains. The receiving trays are mounted on the mounting bars in such a way as to be movable between the front and rear mounting bars in the axial direction of the mounting bars. The guide rails which are located at a lower part of the traveling path of the receiving trays are arranged to allow the guide pins which protrude downward from the lower sides of the receiving trays to travel in a curved manner as the conveyor chains travels. The curved travel of the guide pins is arranged to be made such that the spacing intervals between the columns of the receiving trays become sufficiently wide at the inspection area for installing the light projecting means and the light receiving means there. Therefore, the light projecting means and the light receiving means can be mounted at any desired position, except the path of the mounting bars, and in any desired posture without any space restriction, in such a way as to have the receiving tray located between them.

Further, in the first embodiment, the rows of the receiving trays are arranged to be moved in parallel in such a way as to gradually narrow the spacing intervals between adjacent columns of the receiving trays as they move toward the end of the transport path from the inspection area. Therefore, at the end of the transport, the spacing intervals between the columns of receiving trays can be accurately adjusted to the spacing intervals of the transport means arranged for a next process. By virtue of the arrangement, therefore, the inspection objects can be smoothly and continuously transported by a plurality of transport means.

In the second embodiment, each of the receiving trays which are in a plurality of rows is arranged to have its lower front part in the direction of travel of the conveyor loosely fitted on one of the mounting bar located in front of the receiving tray and also to have its rear side part engage another mounting bar located in rear of the receiving tray. Therefore, the spacing intervals between the front and rear mounting bars can be widely arranged to lower the vertical height of the receiving trays by sinking each of them in a space between the mounting bars. The vertical through hole which is provided as a transmission light passage in the center part of each receiving tray can be arranged to have a wider diameter and a shorter vertical height, so that the quantity of transmission light to be received by the light receiving means can be sufficiently increased.

In the third embodiment, with the through hole vertically formed in the bottom center part of each of the receiving trays and also in its elastic receiving seat to provide a transmission light passage, the light receiving means is arranged to be located close to the lower face of the receiving tray below the receiving tray travel path. This arrangement enables the device to detect even a slight amount of transmission light coming from the inspection object. Besides, the light blocking bottom face which extends forward and rearward from the exit part of the hole effectively prevents disturbance light from entering there. Therefore, the light projecting means can be arranged to project light on the inspection objects from on both the right and left sides of the objects on the receiving trays which are arranged in a plurality of rows and in a plurality of columns. The arrangement of the embodiment thus permits an increase in quantity of light to be projected, so that the internal quality of the inspection object can be easily examined even in case where the inspection object does not readily permit transmission of light therethrough.

The above and other objects and features of this invention will become apparent from the following detailed description of embodiments thereof taken in connection with the accompanying drawings.

DETAILED DESCRIPTION OF THE INVENTION

Some of embodiments of this invention are described in detail below with reference to drawings.

[First Embodiment]

Figure 1:
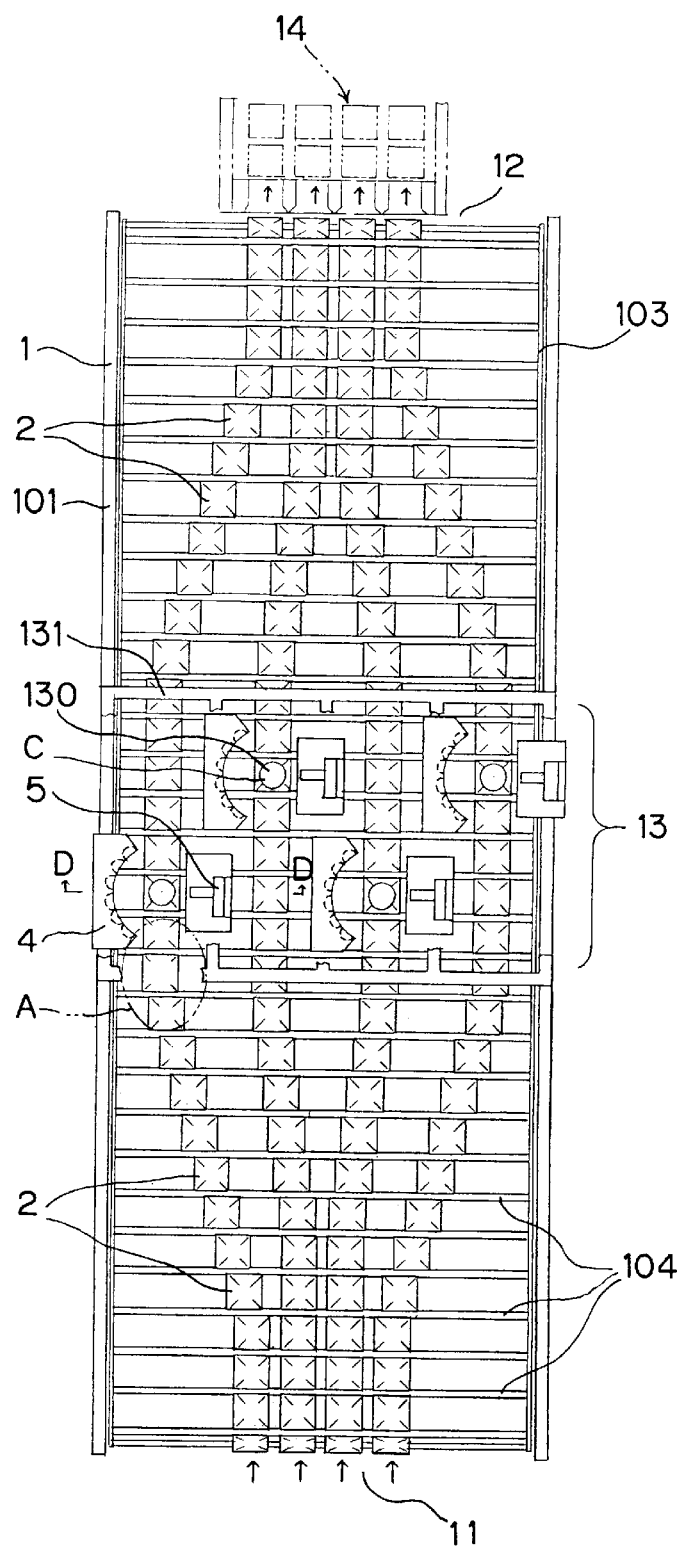
FIG. 1 is a plan view showing an online internal quantity inspection embodying this invention.
Figure 2:
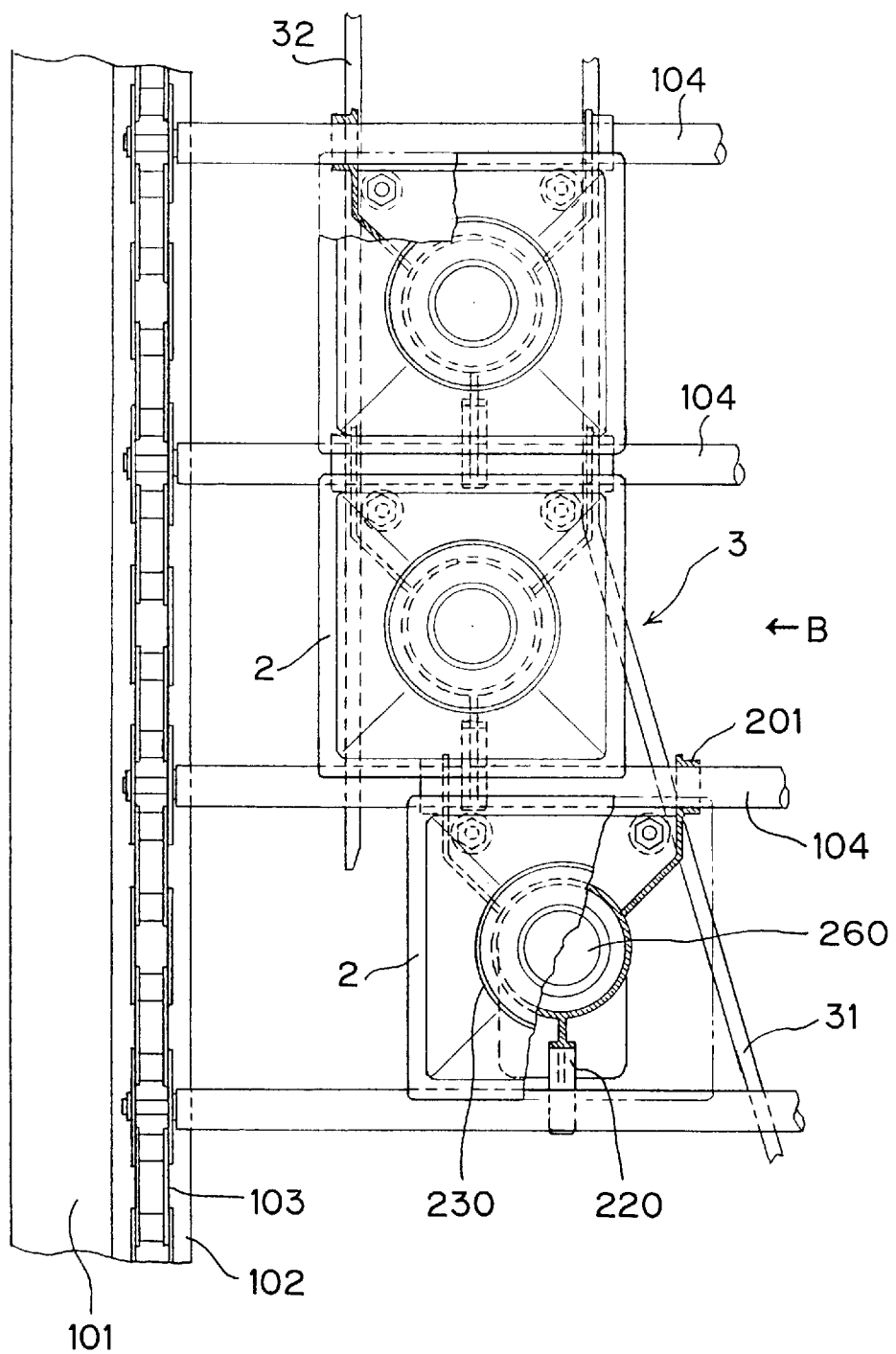
FIG. 2 is a plan view showing essential parts of the same embodiment shown within a circle A in FIG. 1.
Figure 3:
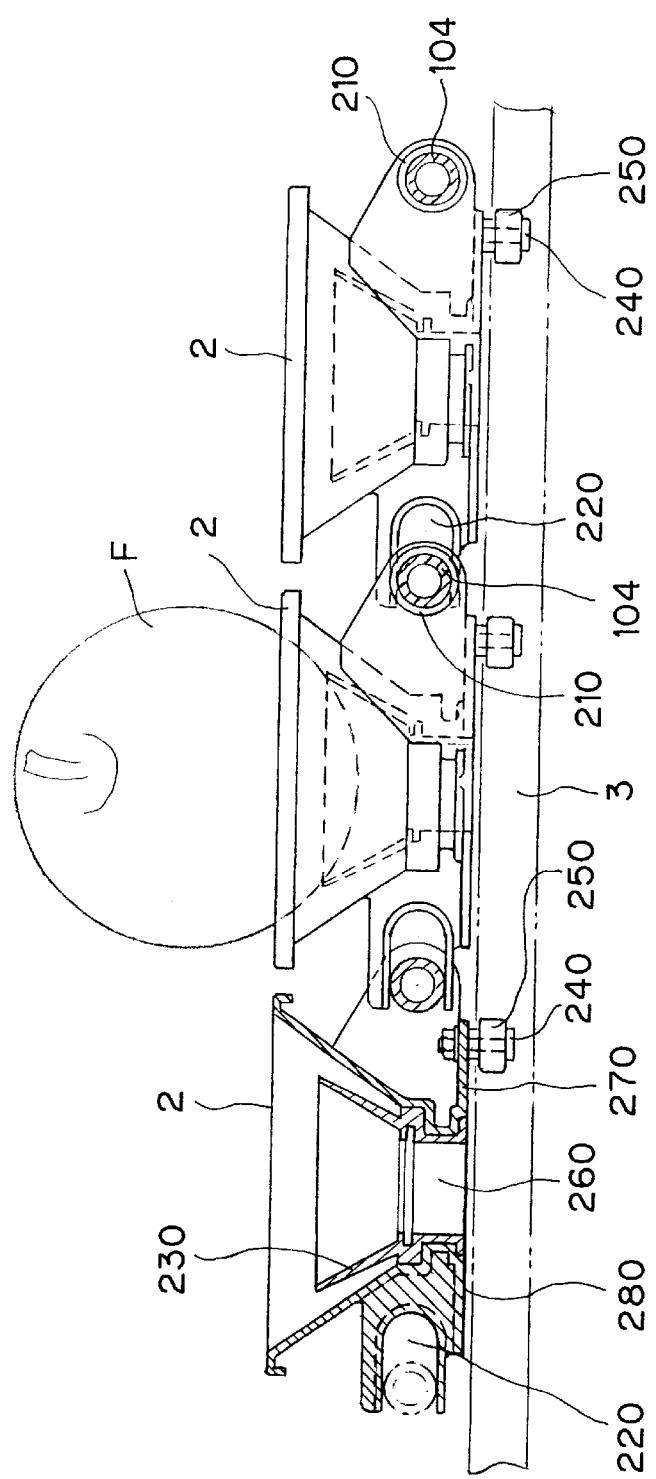
FIG. 3 is a longitudinal side view showing a part of the same embodiment as viewed from the direction indicated by an arrow B in FIG. 2.

FIG. 1 is a plan view showing an online internal quantity inspection device which is arranged according to this invention as a first embodiment thereof. FIG. 2 is a plan view showing essential parts of the embodiment shown within a circle A in FIG. 1. FIG. 3 is a longitudinal side view showing a part of the same embodiment as viewed from the direction indicated by an arrow B in FIG. 2. The details of these parts are as shown in FIGS. 4 to 7.

Referring to the drawings, transport means 1 has two chain rails 102 arranged in parallel with each other on two opposite inner sides of a frame 101. Conveyor chains 103 are endlessly stretched respectively on and along the two chain rails 102. Receiving tray mounting bars 104 are mounted by arranging them in parallel at predetermined spacing intervals in the direction of travel between the conveyor chains 103. With the tray mounting bars 104 arranged in parallel, a plurality of receiving trays 2 (four receiving trays in this case) are arranged in each of a plurality of rows and mounted on the receiving tray mounting bars 104. Each row of the receiving trays 2 is thus carried by the mounting bars 104 between front and rear mounting bars 104 in such a way as to be movable in the longitudinal direction of the mounting bars 104. The receiving trays 2 are thus arranged to be movable in the direction of width of a conveyor.

FIGS. 2 and 3 show the receiving trays 2 in detail. FIG. 3 is a partly sectional view of them. As shown, each of the receiving trays 2 is provided with two loosely fitting parts 210 which extend from an upper front part to a lower part of the tray 2. The mounting bar 104 on the front side of each of the receiving trays 2 is inserted through the loose fitting part 210. The receiving tray 2 also has an inserting cutout part 220 which opens rearward on the rear side of the receiving tray 2. The mounting bar on the rear side of the tray 2 is inserted into this cutout part 220. These parts are thus assembled to maintain each of the receiving trays 2 in a horizontal attitude.

In other words, the mounting bars 104 which are located in front and in rear of each receiving tray 2 are arranged to carry four receiving trays between them in a state of being loosely fitted in the right and left front side loosely fitting parts 210 of each receiving tray 2. Each receiving tray 2 is carried by the mounting bars 104 through the left and right loose fitting parts 210 on its front side and the rear inserting cutout part 220 of the preceding receiving tray 2 in such a way as to be movable in the longitudinal direction of the mounting bars 104. By virtue of this arrangement, the lateral position of each of the receiving trays is shiftable within a range in which the inserting cutout part 220 of the preceding tray 2 is movable between the right and left loosely fitting parts 210 of the following tray 2 as shown in FIG. 2.

As shown in FIG. 1, with the four receiving trays 2 arranged in one row between each pair of front and rear mounting bars 104, a total of four transport columns of receiving trays 2 are formed.

Further, the mounting bars 104 may be arranged to carry the receiving trays in pairs or singly or in any other manner as long as they are arranged to be capable of keeping the receiving trays in a horizontal attitude when the conveyor chains are horizontally traveling.

With the receiving trays 2 arranged in four columns as mentioned above, the columns of them are guided respectively by guide rails 3 which are arranged to be corresponding to them along their traveling path. The guide rails 3 include entrance side spreading guide rails 31. The guide rails 31 are arranged to adjust, at an entrance part 11 of the transport path, the spacing intervals of the receiving tray columns to the spacing intervals of the transport columns of a supply device of a preceding process (not shown); and then to widen and spread the spacing intervals according as the receiving trays 2 travel toward an inspection area 13 which is provided at an intermediate part of the transport path. The spacing intervals at the inspection area 13 are wide enough to arrange light projecting means 4 between the columns of the receiving trays to project light rays on inspection objects F from on one side of them with the inspection objects F set on the receiving trays 2. Light receiving means 5 is arranged, in combination with the light projection means 4, to receive a transmission light through the inspection objects F. After the inspecting area 13, the spacing intervals are gradually narrowed as the receiving trays travel toward an exit part 12 by exit side narrowing guide rails 32 to adjust the spacing intervals to the column spacing intervals of a sorting conveyor 14 connected to a subsequent process.

In short, the spacing intervals among transport path columns of the receiving trays 2 are arranged to be in a shape spreading wider at an intermediate part of the transport path.

Each of the receiving trays 2 is provided with an elastic receiving seat 230, which is disposed inside of the receiving tray 2 for stably setting the inspection object F thereon. The receiving tray 2 is provided also with a guide pin 240, which protrudes downward from the lower side of the receiving tray 2. The guide pin 240 is preferably provided with a guide roller 250 for the purpose of mitigating contact friction with the guide rail 3. However, in case where the receiving tray 2 can be laterally moved without much load, the guide pin 240 does not have to be provided with the guide roller 250. Each receiving tray 2 may be provided with only one guide pin 240 with or without the guide roller. However, it is preferable to arrange each receiving tray 2 to have right and left guide pins 240 with the guide rollers 250 to ensure that the receiving tray 2 can be smoothly moved in the lateral direction to the right or to the left as the conveyor travels further. Further, it is also preferable to have the guide pins 240 which are to be guided by the guide rails 3 are made of resin material for reduction in frictional resistance taking place between the guide pins 240 and the guide rails 3.

Figure 5:
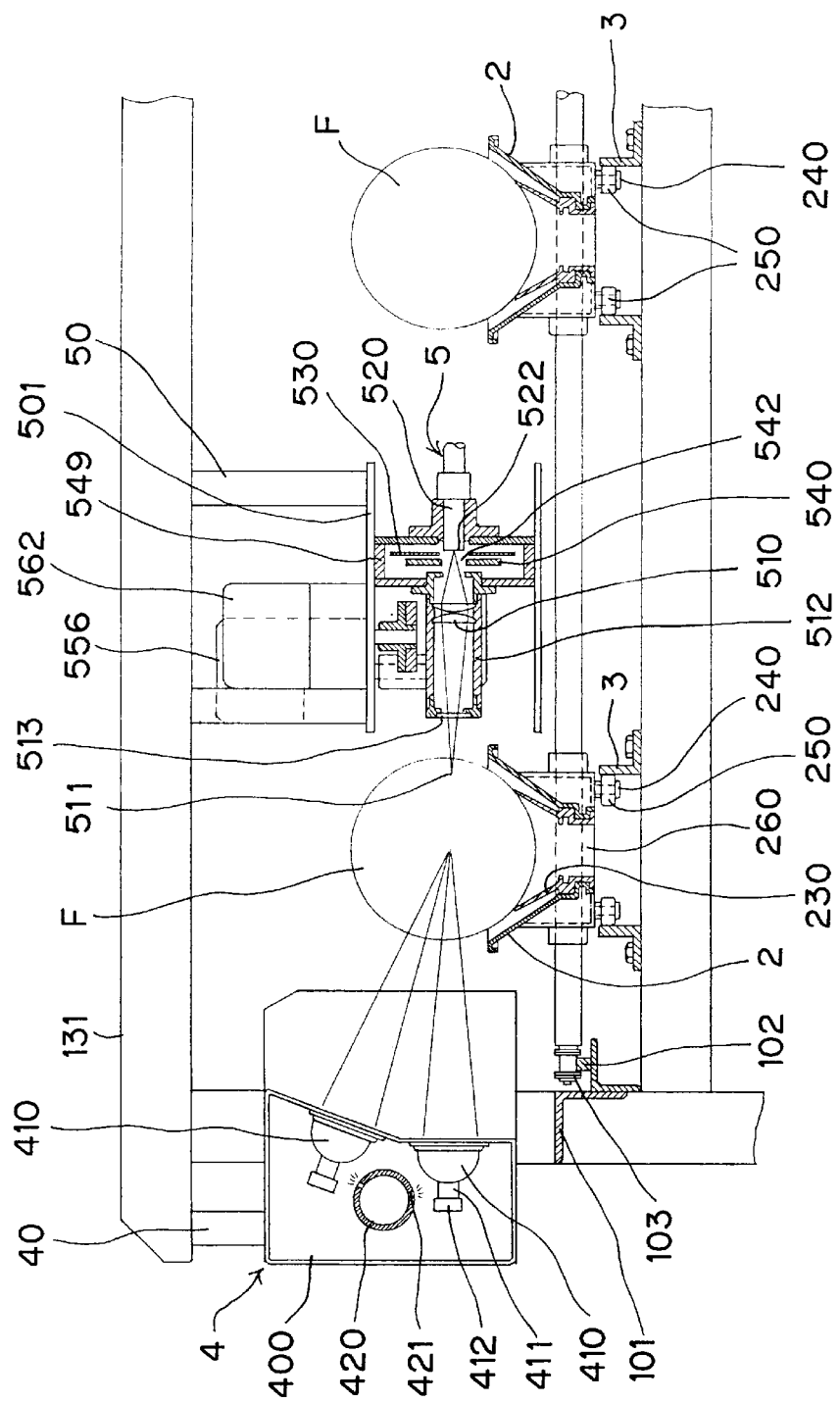
FIG. 5 is a front and longitudinal sectional view showing parts at the inspecting position indicated by a symbol D in FIG. 1.
Figure 6:
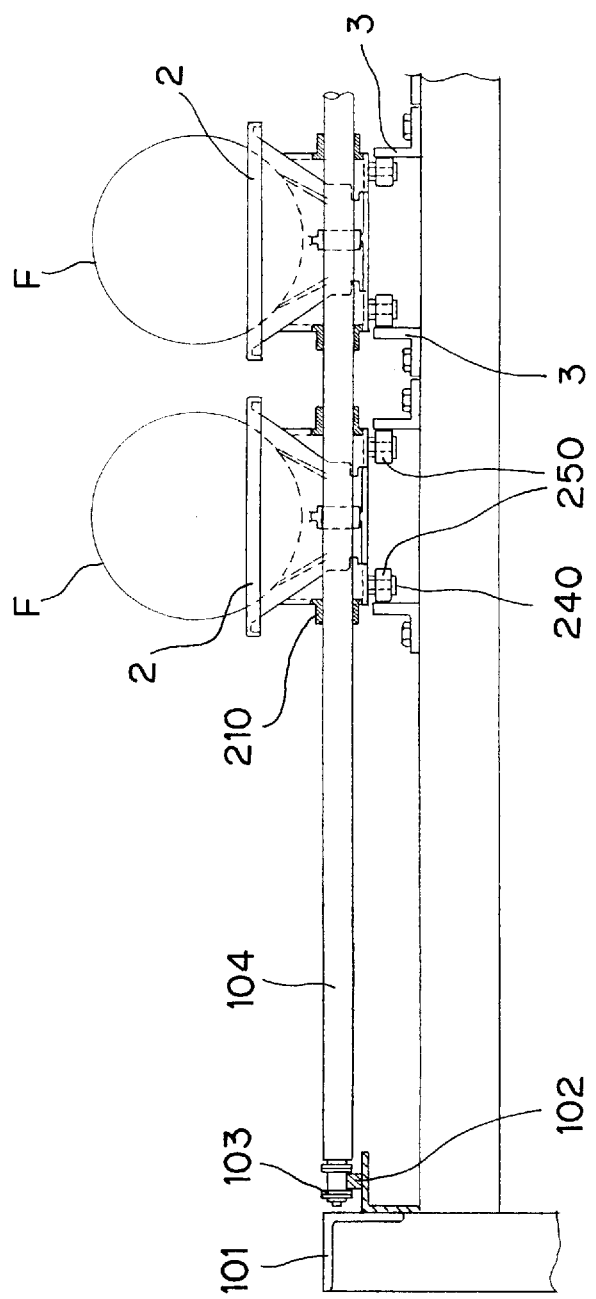
FIG. 6 is a front view showing the embodiment as in a state obtained with spacing intervals narrowed on the entrance and exit sides of a transport path.

As shown in FIGS. 3 and 5 which are longitudinal sectional views, the elastic receiving seat 230 is in a shape of inverse circular cone and is combined with each receiving tray 2 by fitting it into the later. Each of the elastic receiving seat 230 is preferably arranged to have a hole 260 vertically penetrate the center part of its bottom side, though the bottom side may be formed without the hole 260. In this case, the hole 260 is provided with light blocking bottom faces 270 and 280 which are arranged to horizontally extend in front and in rear of the exit side of the hole 260.

The light blocking bottom faces 270 and 280 effectively prevent the light receiving means 5 from being affected by disturbance light. In addition to this, when a spectroscopic analyzer which is used for the internal quality inspection through a transmission light obtained from the light receiving means 5 happens to be affected by variations in ambient temperature or by aging, the light blocking bottom faces 270 and 280 can be used for zero level calibration. More specifically, a zero level is detected and calibrated either immediately before or immediately after arrival of the exit part of the passage of transmission light of the receiving tray 2. After the calibration, the transmission light is detected while the exit part of the transmission light passage is passing above the light receiving means. This arrangement enables the internal quality inspection by spectroscopic analysis to be stably carried on all day from morning till evening.

The lower part on the front side of each of the receiving trays 2 is loosely fitted on the mounting bar 104 to be movable right and left. The inserting cutout part on the rear side of the receiving tray 2 has another mounting bar located in rear of the receiving tray 2. Each receiving tray 2 is thus arranged to horizontally travel. Further, the spacing intervals between front and rear mounting bars are arranged to be wide open to allow the receiving trays 2 to sink in a space between the mounting bars 104 and to lower their vertical height. Besides, the hole which serves as the transmission light passage is formed to be large. With the light receiving means arranged to be in an upward posture below the receiving tray traveling path, the embodiment is capable of detecting even a weak transmission light passing through the inside of such an inspection object that does not readily transmit light due to its size or a thick skin. The result of detection becomes better as the hole diameter of the transmission light passage is larger and the optical path length of the device is shorter.

The supply part of the transport path may be arranged to cause spacing intervals between the plurality of columns of the receiving trays to be narrowed by moving them to gather toward one side of the conveyer at the start end of the transport path; and to allow the columns of the receiving trays to travel a predetermined distance in this state in parallel with each other in such a way as to have the inspection objects supplied by human hands from one side of the conveyor. With the supply part thus arranged, the spacing intervals between the columns of the receiving trays are arranged to be gradually widened between the supply part and the inspection area. By this arrangement, the position of the inspection objects can be smoothly shifted from a preceding process to the invented multi-row type internal quality inspection device without recourse to an automatic supply device.

In the case of the above-stated arrangement, in narrowing the spacing intervals between the columns of the receiving trays for connecting them at the exit end part of the transport path to a subsequent process, these columns either may be arranged to be gathered at the center part of the transport conveyor or may be arranged to be shifted together toward one side of the conveyor.

The elastic receiving seat 230 is preferably formed in the shape of a frustum of inverse circular cone, a bowl shape, a funnel shape or the like which stabilizes each inspection object by absorbing a placing impact by its elasticity when the inspection object is placed on the receiving tray 2. The elastic receiving seat 230, however, may be in any other suitable shape so long as it ensures the desired stabilizing effect.

Figure 7:
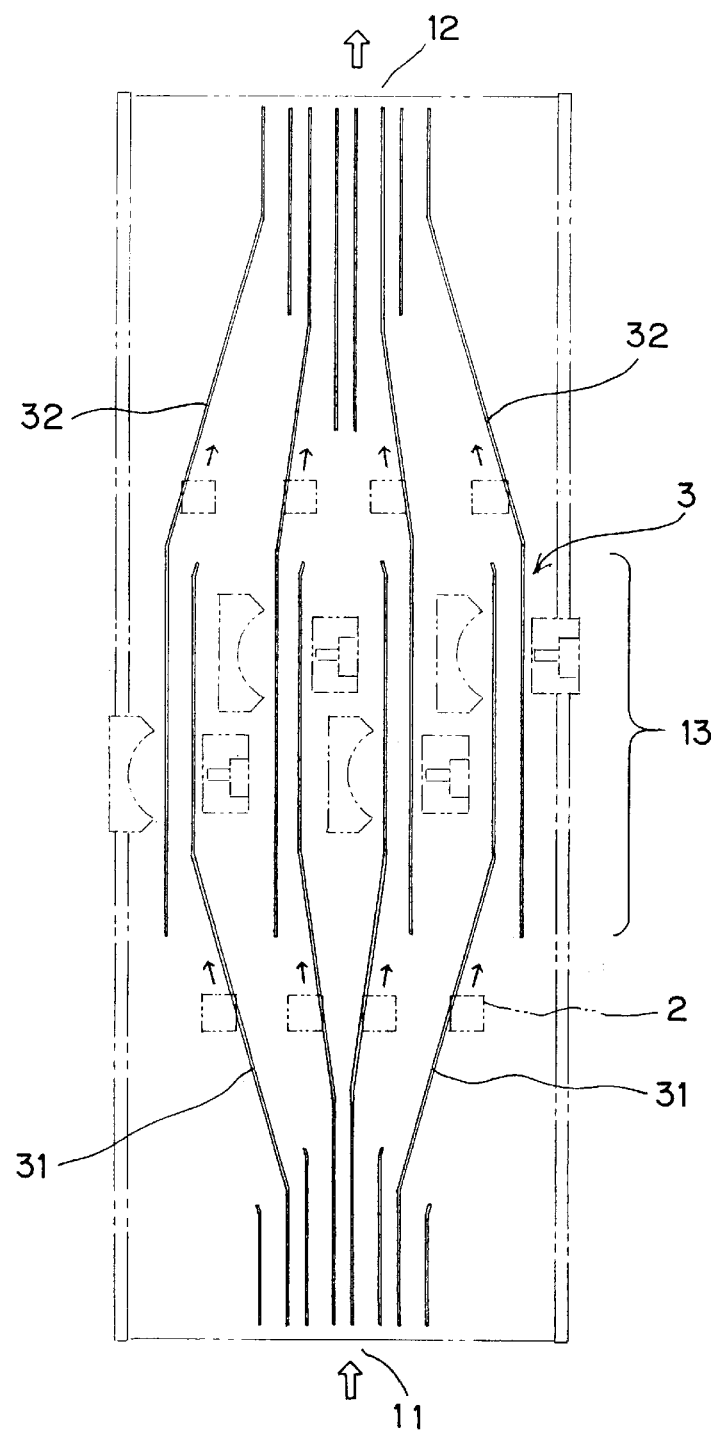
FIG. 7. is a plan view showing guide rails which form a traveling path of receiving trays shown in FIG. 1.

The guide rails 3 are arranged as shown in FIG. 7. As shown, the entrance-side spreading guide rails 31 are arranged to guide the columns of the receiving trays 2 to cause the spacing intervals between the receiving tray columns to become wider as they travel from the entrance part 11 to the inspection area 13. The exit-side narrowing guide rails 32 are arranged to cause the spacing intervals between the receiving tray columns to become narrower as they travel from the inspection area 13 to the exit part 12. In other words, the guide rails are arranged to move receiving trays 2 as follows: While the receiving trays 2 are traveling in columns, the space intervals between the columns are spread wide at the inspection area and are again narrowed at the exit part.

Figure 4:
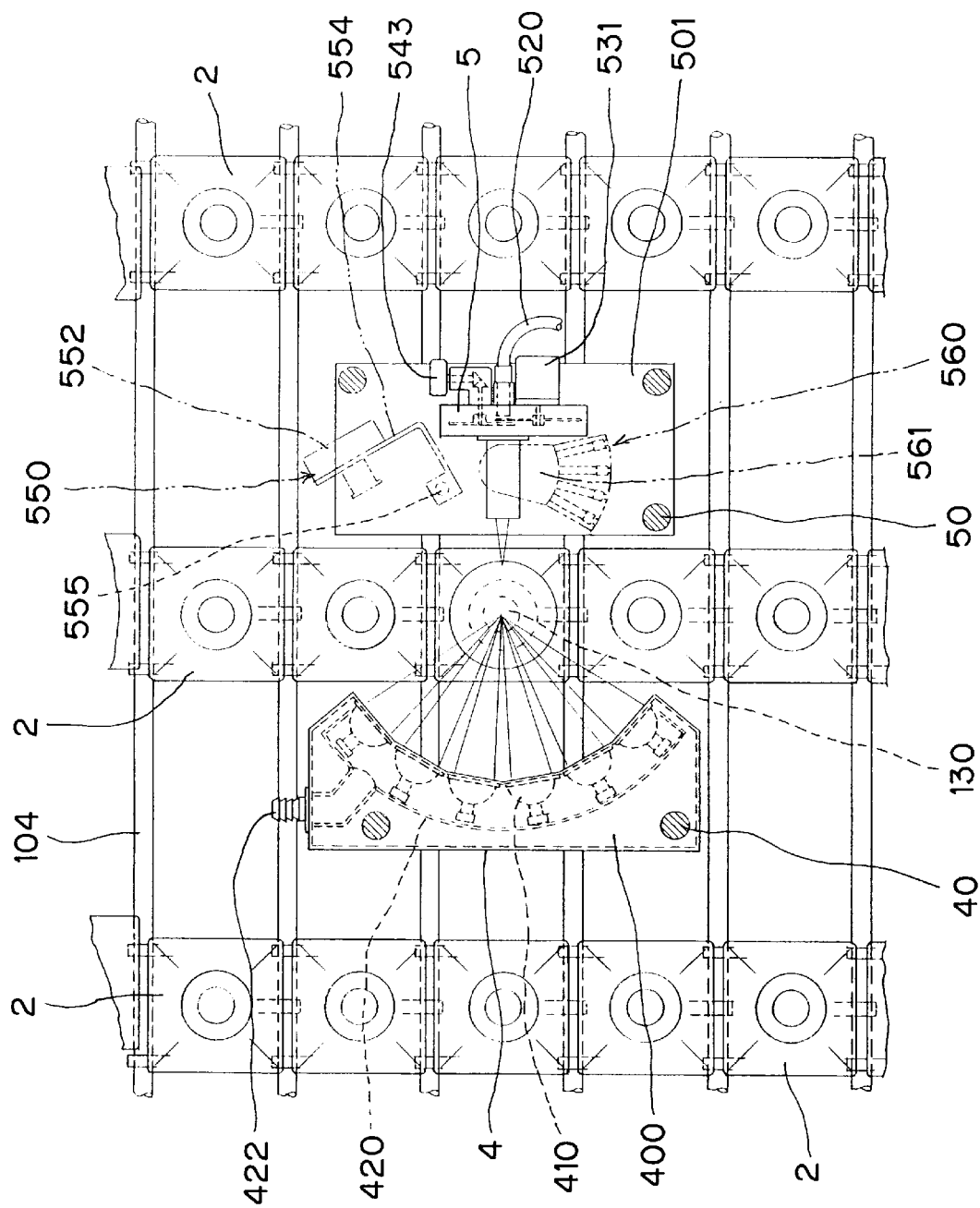
FIG. 4 is a plan view showing essential parts at and around an inspecting position indicated by a symbol C in FIG. 1.

The light projecting means 4 and the light receiving means 5 are arranged as shown in FIGS. 4 and 5. As shown, at the inspection area, the light projecting means 4 and the light receiving means 5 are mounted through brackets 40 and 50 on a mounting frame 131 in a state of being opposed to each other across the inspection objects F which are placed on the receiving trays 2.

Each light projecting means 4 is provided with a lamp box 400 in which many halogen lamps 410 are arranged to concentratedly project light rays toward the center of the inspection object from different positions within a range from an oblique front point to an oblique rear point of each inspection object F with the inspection object F on the receiving tray 2 conveyed to a preset inspecting position 130 within the inspection area 131. The halogen lamps 410 are relatively small and preferably are in the form of a front sealed lamp having a parabolic reflection mirror which is formed at a beam angle at which a focal point is obtained at the inspecting position 130.

The positions of these many halogen lamps 410 are preferably arranged in a sectorial shape to be at equal spacing distances from the center of the inspection object on the receiving tray 2 at the inspecting position 130.

Referring to FIGS. 4 and 5 in particular, a radiator duct 420 is arranged for the halogen lamps 410 to extend along the sectorial aligned positions of sealing parts 411 and sockets 412 of the halogen lamps 410. The radiator duct 420 is provided with air blowing nozzles for blowing air at the sealing parts 411 of the halogen lamps from an air blower (not shown) which is connected to a connection hole 422 by some suitable air supply means. The sealing part 411, the socket 412 and the lamp body of each halogen lamp 410 are thus prevented from being overheated by diffusing the heat generated by them.

Each light receiving means 5 comprises essential parts including a condenser lens 510; an optical fiber 520 arranged to cause a transmission light which is converged by the condenser lens 510 to be guided to a spectroscope (not shown); a shutter 530 arranged to cover the light entry plane 522 of the optical fiber 520; a light-reducing-filter mounting plate 540; a white level calibrator 550; and a reference substance inserting device 560. These essential parts are mounted on a mount base 501. The condenser lens 510 is arranged to have a focal point 511 at a peripheral point of the inspection object F on the receiving tray 2 and is provided with a cylindrical lens hood 512 which extends close to the inspection object F; and a light receiving window 513 having a transparent glass piece used in front of it. The lens hood 512 serves to ensure efficient incidence of the transmission light coming from the front within a field defined by the light receiving window 513 by preventing the adverse effect of disturbance light around the condenser lens 510. The optical fiber 520 is mounted by adjusting its entrance light plane 522 to the imaging position of the condenser lens 510. The transmission light incident on the condenser lens 510 from the light receiving window 513 is imaged on the light entry plane 522. Then the spectroscope connected through the optical fiber 520 is used to carry out spectroscopic analysis on the transmission light.

The shutter 530 is preferably disposed near the imaging position where the transmission light is converged and focused by the condenser lens 510, i.e. the light entry plane 522 of the optical fiber 520. The shutter 530 is arranged to open when the center part of the inspection object F is caused to pass the inspection position 130 by a stepping drive device 531, which is arranged to cause each of the inspection objects F to stop at a predetermined position by driving the object F by inches. The shutter 530 closes when the inspection part (such as a center part) of the inspection object F is caused to pass through the inspection position by the inching driving action of the stepping drive device 531.

Figure 9:
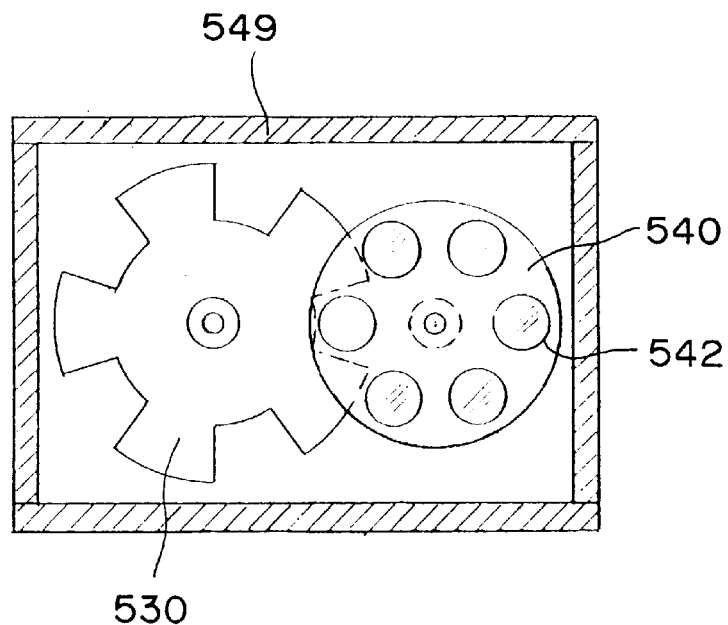
FIG. 9 is a detail view showing relation between a shutter and a light reducing filter mounting plate as in a state obtained when light is not blocked.
Figure 10:
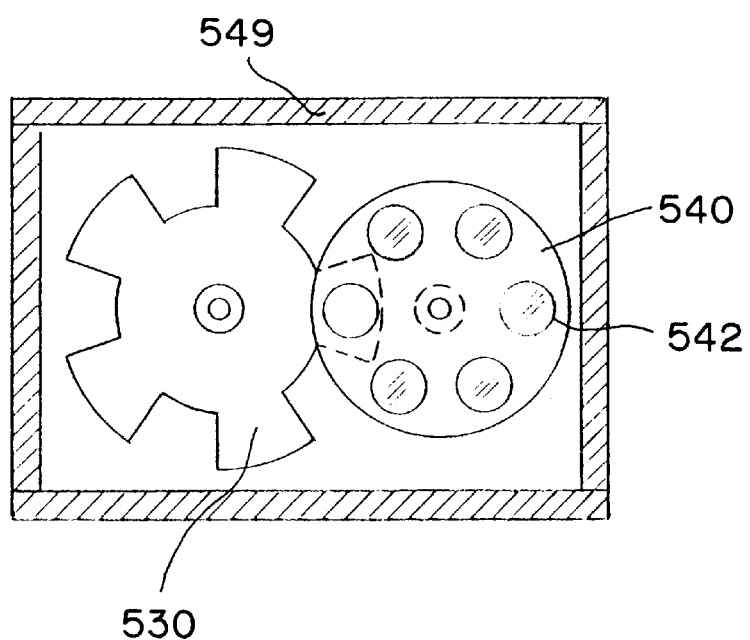
FIG. 10 is a detail view showing the relation between the shutter and the light reducing filter mounting plate as in a state obtained when light is blocked.

Referring to FIGS. 9 and 10, the light-reducing filter mounting plate 540 is in a disk-like shape and is mounted on a shaft disposed on one side of the optical fiber 520. The disk-like light-reducing filter mounting plate 540 is large enough to block the transmission light to be imaged on the light entry plane of the optical fiber 520. With the shaft at the center of the filter mounting plate 540, a plurality of filter mounting holes 542 are arranged and evenly spaced in a circle having its radius extending from the center shaft to the center of the optical fiber 520. One of the filter mounting holes 542 is left blank while light reducing filters 544 having different light reducing rates are mounted respectively on other filter mounting holes 542. The positions of these filter mounting holes 542 are arranged to be selectable by turning a knob handle provided outside of the device to rotate a shaft mounted through a miter gear 545.

The shutter 530 and the light-reducing-filter mounting plate 540 encompassed with a box 549 which forms a dark room to prevent any adverse effect of disturbance light on the device.

Figure 8:
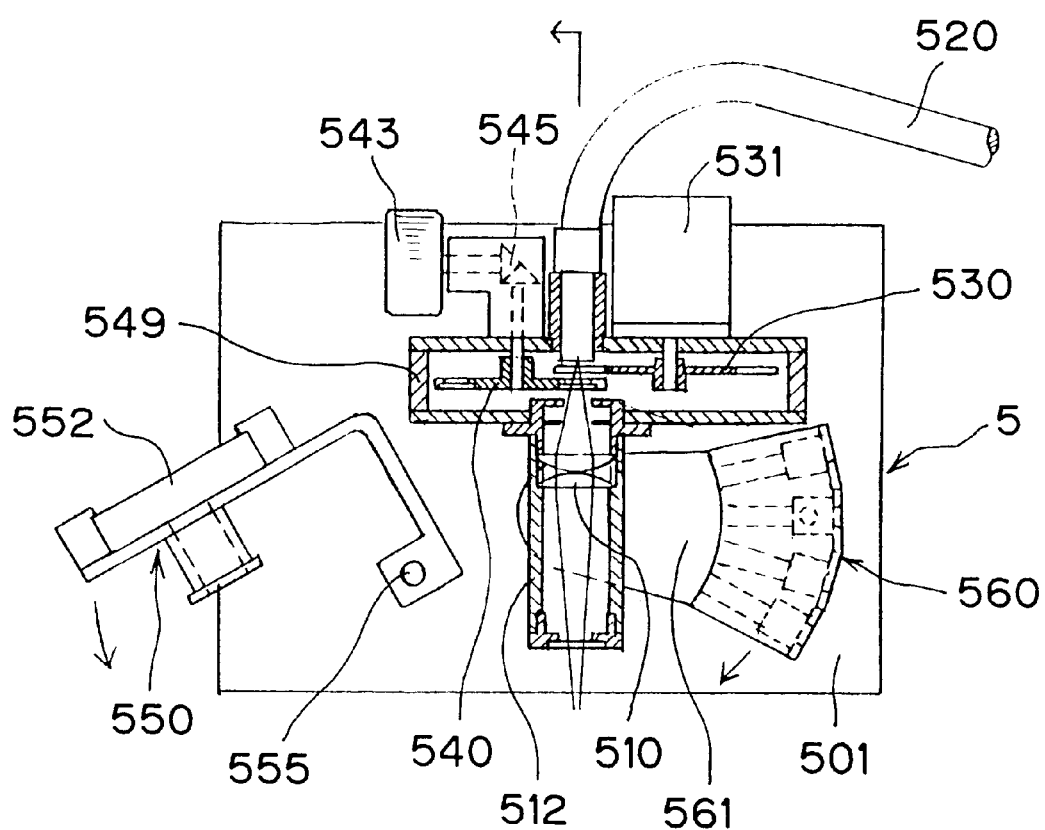
FIG. 8 is a partly sectional plan view showing the arrangement of light receiving means.

In FIGS. 4 and 8, the white level calibrator 550 and the reference substance inserting device 560 are shown at their non-operating positions. The white level calibrator 550 has a white level calibrating plate 552 mounted on a mounting arm 554. The mounting arm 554 is mounted on a mount base 501 and is swingable on the rotating shaft 555 of a stepping motor 556 shown in FIG. 5 by using the driving force of the stepping motor 556. For example, the white level calibrating plate 552 can be moved to or retracted from the front of the lens hood 512 of the condenser lens 510 by causing the stepping motor 556 to rotate forward or backward.

The quality reference substance inserting device 560 includes a plurality of reference (substance) vessels 562 which are made of transparent quartz glass. These vessels 562 respectively contain therein sugar or acid solutions of various concentrations arranged to have a high sugar concentration, a low sugar concentration, a high acidity, a low acidity, etc. The reference vessels 562 are mounted on a sectorial mounting arm 561 formed to stand in front of the lens hood 512 of the condenser lens 510 in such a way as to have the peripheral face of each of reference vessels come to the position of the focal point 511 of the condenser lens 510 on the object side. The sectorial mounting arm 561 is mounted on the output shaft of the stepping motor 562 which is carried by the mount base 501 and is thus positioned above the outer side of the lens hood 512 of the condenser lens 510.

The quality reference substance inserting device 560 is normally operated for correcting an analytical curve of spectral analysis after a calibrating operation on the white level calibrator 550. However, the quality reference substance inserting device 560 is operated as necessary according to the environmental variations in respect of temperature, humidity, etc. or the lapse of time and is retracted on one side of the condenser lens 510 when no calibrating operation is performed.

The quality reference substance does not have to be used in a liquid state of solution but may be used in a gel state or in a solid state.

[Second Embodiment]

Figure 11:
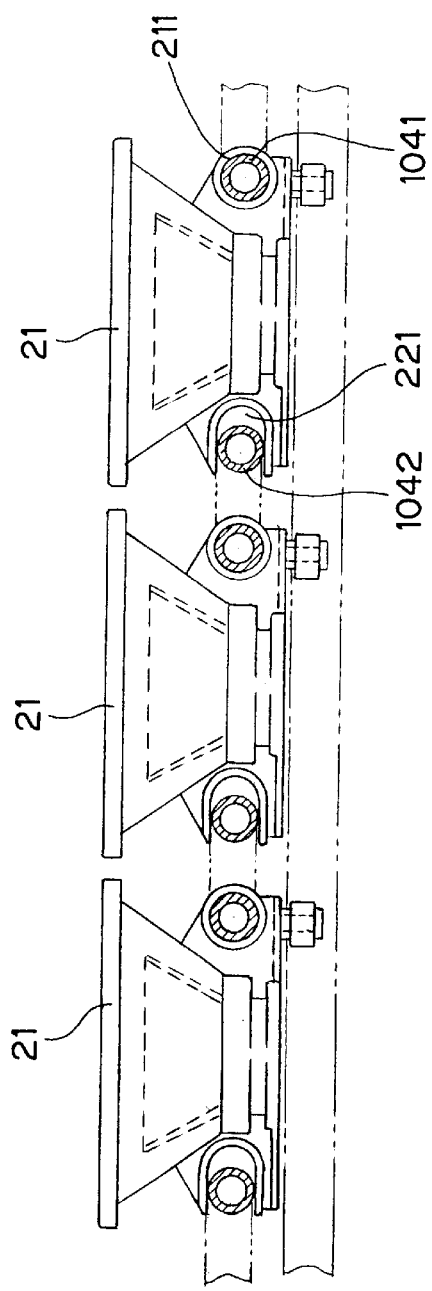
FIG. 11 is a side view showing the receiving trays of a second embodiment of this invention as in a state of having each of the trays supported by front and rear mounting bars.

FIG. 11 shows a second embodiment of the multi-row type online internal quality inspection device of this invention. Referring to FIG. 11, each of receiving trays 21 is arranged to be supported jointly by front and rear mounting bars 1041 and 1042. The receiving tray 21 is provided with left and right loose fitting parts 211 which are disposed at lower front parts of the receiving tray 21 and have the front mounting bar 1041 passing through them. The receiving tray 21 also has inserting cutout parts 221 which open rearward on the rear side of the receiving tray 21 at positions corresponding to the positions of the loose fitting parts 211. The rear mounting bar 1042 is inserted into the inserting cutout parts 221 in such a way as to keep each receiving tray 21 at a horizontal attitude. The inserting cutout parts on the rear side may be formed in a slot-like shape.

The above-stated arrangement of the second embodiment has an advantage in that each of the receiving trays 21 can be laterally moved without any interference with other trays located in front and in rear thereof. Therefore, for each of the processes of gradually widening and narrowing the spacing intervals between columns of the receiving trays before and after the inspection area, the arrangement permits reduction in traveling distance of the receiving trays in the narrowing or widening process.

[Third Embodiment]

Figure 12:
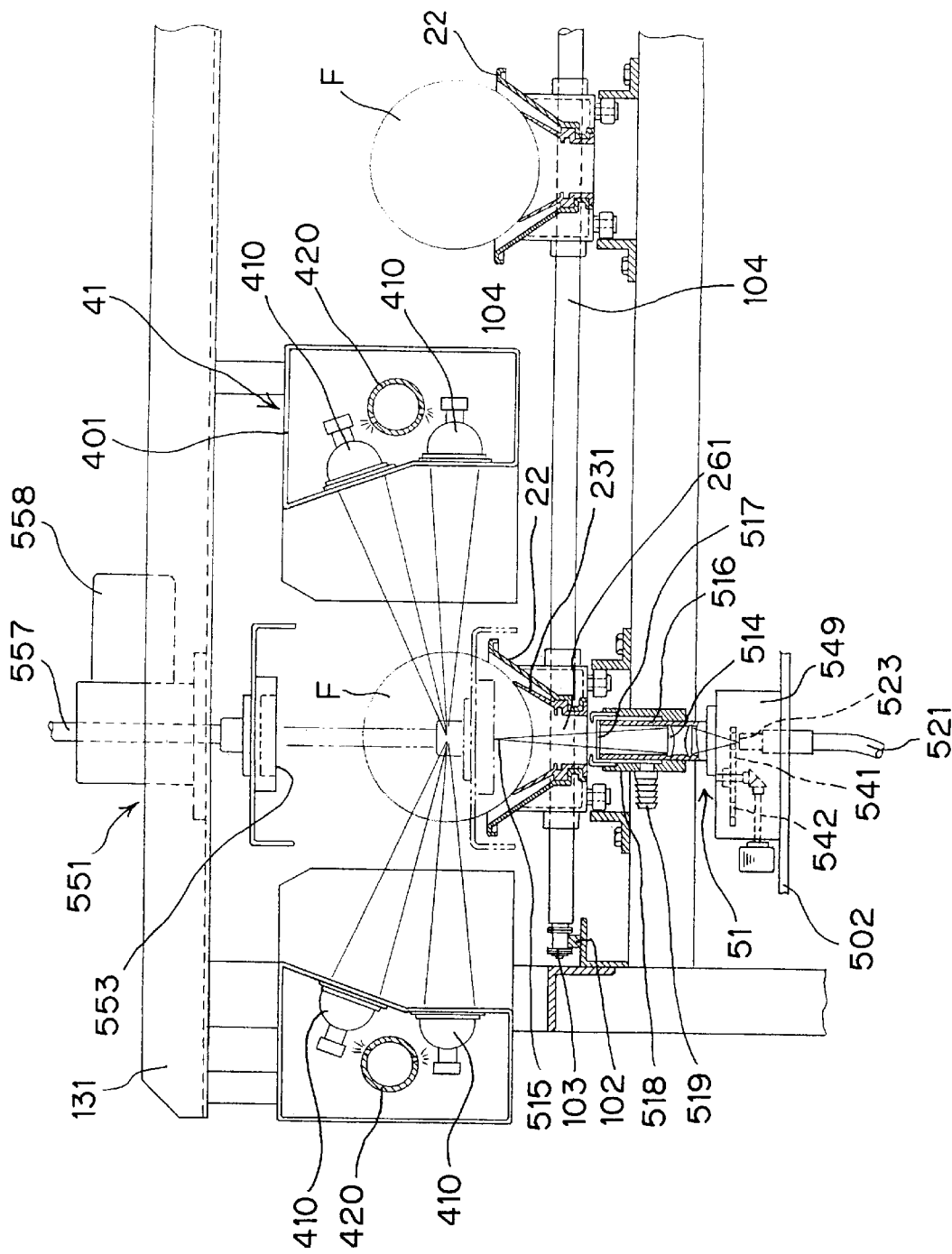
FIG. 12 is a front and longitudinal sectional view showing light receiving means of a third embodiment of this invention as in a state of being set directly below the receiving tray at the inspecting position.

FIG. 12 shows a third embodiment of the multi-row type online internal quality inspection device according to this invention. In the third embodiment, the arrangement and the allocation of light projecting means 41 and light receiving means 51 at the inspection area differ from the arrangement of the light projecting means 4 and the light receiving means 5 of the first embodiment. Referring to FIG. 12, the light projecting means 41 of the third embodiment is arranged to have two lamp boxes 401 which are disposed on both the left and right sides of the inspection object F on each of the receiving trays 22 and are of structural arrangement similar to that of the light box of the first embodiment. With the light boxes 401 thus arranged, the light rays can be concentratedly projected toward the center of the inspection object F from different positions and at different angles within a range from an obliquely front part to an obliquely rear part of the inspection object F on each of the front and rear sides thereof.

The light receiving means 51 is mounted on a mount base 502 in an upward facing posture immediately below the receiving tray 22 at the inspection area 130. More specifically, the rays of light are arranged to be concentratedly projected on the inspection object F from both the right and left sides thereof. A through hole 261 is formed to vertically penetrates an elastic receiving seat 231 which is disposed inside of each of the receiving trays 22. The light receiving means 51 is arranged to detect a transmission light coming through the inside of the inspection object on the receiving tray 22 and also through the through hole 231 when the rays of light are concentratedly projected on the object F from on the right and left sides of the object F. The light receiving means 51 is mainly composed of a condenser lens 514; an optical fiber 521; and a light-reducing-filter mounting plate 541 which is disposed in front of the light entry plane 523 of the optical fiber 521. The main components of the inspection device are prevented from any adverse effect of disturbance light by encompassing them with a box body 549 which is arranged to form a dark room.

The condenser lens 514 is arranged to have its focal point 515 at a lower surface part of the inspection object F on the receiving tray 22 through the through hole 261 in the center part of the receiving tray 22 with the receiving tray 22 at the inspection position 130. The condenser lens 514 is provided with a cylindrical lens hood 516 which extends close to the lower side of each receiving tray 22; and a light receiving window 517 which has a transparent glass disposed in front thereof. A dust proof hood 518 is arranged in combination with the lens hood 516 to blow in air through a clearance between the periphery of the lens hood 516 and the inner side of the dust proof hood 518 from the peripheral part of the lens hood 516 toward the center part of the external side of the light receiving window 517. The dust proof hood 518 is mounted to have its upper end face as close as possible to the lower face of the receiving tray 22. For the air blowing action, an air blower (not shown) is connected by suitable means to an air connection port 519.

With the lens hood 516 arranged to face upward below each of the receiving trays 22 which it comes on the conveyor, air is thus blown at the light receiving window 517 to remove and prevent dust and foreign matters from blocking the field of view. The lens hood 516 is arranged to block all disturbance light coming from around it and thus to efficiently allow only such transmission light that comes from the front within the field of view which is defined by the light receiving window 517.

The optical fiber 521 has its light entry plane 523 adjusted to the imaging position of the condenser lens 514 to cause the transmission light incident on the condenser lens 514 through the light receiving window 517 to be imaged on the light entry plane. The optical fiber 521 then leads the transmission light to a spectroscope which is not shown but is arranged to conduct spectrum analysis. A filter mounting plate 541 is in a disk-like shape and is large enough to block the transmission light imaged on the light entry plane of the optical fiber 521. The filter mounting plate 541 is mounted on a shaft 542 which is provided on one side of the optical fiber 521. The filter mounting plate 541 is provided with filter mounting holes which are arranged at equally spaced positions in a circle having the shaft 542 at its center and its radius at the center position of the light entry plane 523 where the transmission light is to be imaged. Light reducing filters of different light reducing rates are mounted on these filter mounting holes. One of these filters are selected by means of an external knob handle in the same manner as in the case of the first embodiment described in the foregoing. Therefore, the details of a filter selecting action are omitted from description.

A white level calibrator 551 is disposed above the receiving tray 22 with the receiving tray 22 at the inspection position 130. The white level calibrator 551 is thus arranged at a position which is opposed to the light receiving means 51. The white level calibrator 551 is composed of a white level calibration plate 553, a mounting shaft 557 and a linear motor 558 which is arranged to move the calibrator 551 upward and downward.

A calibrating operation is performed by lowering the calibration plate 553 to cover the upper surface of the receiving tray 22 when the tray 22 is empty. When the calibrating operation is not required, the calibration plate 553 is retracted upward from the transport path.

The first, second and third embodiments of this invention described have the following advantages:

In the first embodiment, the receiving trays which are slidably carried by the mounting bars are arranged in many rows and columns. At the start end part on the entrance side of the conveyor, the spacing intervals of the columns of the receiving trays are adjusted to the spacing intervals of receiving tray columns of a supply device which is arranged to be supplied with inspection objects also in a plurality of columns extending from a preceding process. Therefore, the embodiment can be easily connected to an existing supply device by adjusting its conveyor formation to that of the existing device. It is another advantage that, since the column forming intervals between laterally adjacent receiving trays in the same row can be widened to any distance required at the inspection area for installing each combination of light-projecting and receiving means necessary for inspection of the inspection objects. Therefore, even in case where light transmission is not always easy due to variations in size and skin thickness of inspection objects, their internal quality can be accurately inspected. Further, at the exit end part of the conveyor, the widened column intervals are narrowed to adjust them to the spacing intervals of columns arranged on a sorting conveyor which is provided for a next process. The inspection objects thus can be smoothly sent out to the sorting conveyor. The arrangement of the multi-row type online internal quality inspection device according to this invention thus permits the device to be installed and used by utilizing the existing facilities, such as a supply device and a sorting conveyor, as they are. The invented arrangement, therefore, economizes the facilities to a great extent.

A further advantage of the embodiment lies in the following point: The receiving trays are arranged to travel under the guidance of the guide rails which are provided in the lower part of the path of travel of the receiving trays. Therefore, the columns of the receiving trays not only can be arranged to be moved closer to each other toward the center of the frame at the start part on the entrance side and at the end part on the exit side, as in the case of the first embodiment, but also can be arranged to be moved toward one side.

In the second embodiment of this invention, the loose fitting parts are provided at a lower part of each of the receiving trays on its front side in the direction of travel of the conveyor. The loose fitting parts are loosely fitted on the front mounting bar. Meanwhile, the inserting cutout parts are provided on the rear side of each of the receiving trays. The inserting cutout parts are arranged to engage the rear mounting bar. By virtue of the arrangement, the receiving trays can be kept in a horizontal attitude while the conveyor is horizontally traveling. The arrangement not only permits the inspection objects to be stably conveyed but also effectively lessens a conveyor driving load.

In the third embodiment, the hole vertically penetrating through the center of each of the receiving trays serves as a passage for the transmission light. The light receiving means is arranged to be near to the bottom back face of each of the receiving trays when the receiving tray comes to the inspection position at the inspection area. The light receiving means, therefore, can obtain, from the through hole, the transmission light in a convergent state. The embodiment thus can detect even a slight quantity of transmission light from each of the inspection objects without being affected by disturbance light. Besides, since the light projecting means is arranged on both right and left sides of the inspection object on the receiving tray to project light in a greater quantity on the object, the internal quality of the inspection object can be accurately inspected even if the object does not readily allows light to be transmitted therethrough.

Further, the light blocking bottom face arranged in front and in rear of the exit hole of each of the receiving trays serves as a shutter to cover the front light receiving window of the condenser lens. The light blocking bottom face not only prevents the adverse effect of disturbance light but also permits zero level calibration of the spectroscope to be automatically carried out against variations in ambient temperature and fluctuations due to aging. The multi-row type internal quality inspection device according to this invention, therefore, can be stably operated continuously over a long period of time.

What is claimed is:

1. A multi-row type online internal quality inspection device comprising:

transport means for conveying a plurality of inspection objects in a plurality of rows, said transport means including an inspection area;

light projecting means arranged at predetermined positions in said inspection area to project light rays on the inspection objects set side by side in each of said rows and conveyed by said transport means;

light receiving means arranged at said inspection area to receive transmission light coming through said inspection objects, wherein said transport means comprises a conveyor having left and right conveyor chains endlessly arranged to circularly travel in parallel on left and right sides of said transport means along chain rails;

a plurality of mounting bars arranged in parallel with each other and spaced at a predetermined interval in the direction of travel of said conveyor, two ends of each of said mounting bars being held by said conveyor chains on the left and right sides of said transport means;

a plurality of receiving trays carried by said mounting bars to be shiftable by said mounting bars in parallel with said mounting bars and arranged in a plurality of columns spaced in the direction of width of said conveyor and in a plurality of rows arranged in the direction of travel of said conveyor, and a plurality of guide rails arranged to guide said receiving trays so as to vary a spacing interval between adjacent columns of receiving trays in the direction of width of said conveyor.

2. A multi-row type online internal quality inspection device comprising:

transport means arranged to convey many inspection objects in a plurality of rows and to include an inspection area;

light projecting means arranged in predetermined positions at said inspection area to project light rays on the inspection objects set side by side in each of said rows and conveyed by said transport means; and light receiving means arranged at said inspection area to receive transmission light coming through said inspection objects, and wherein said transport means includes a conveyor having left and right conveyor chains endlessly arranged to circularly travel in parallel on left and right sides of said transport means along chain rails;

a plurality of mounting bars arranged in parallel with each other and spaced at predetermined intervals in the direction of travel of said conveyor, two ends of each of said mounting bars being held by said conveyor chains on the left and right sides of said transport means;

a plurality of receiving trays carried by said mounting bars to be shiftable by said mounting bars in parallel with said mounting bars and arranged in a plurality of columns spaced in the direction of width of said conveyor and in a plurality of rows arranged in the direction of travel of said conveyor, said receiving trays being provided with guide pins which protrudes downward; and a plurality of guide rails arranged to guide said guide pins of said receiving trays to move said receiving trays of each row in parallel with said mounting bars in such a way as to have said receiving trays of each row come closer to each other by narrowing spacing intervals between adjacent columns of receiving trays at a transport start end of said conveyor, to gradually make the receiving tray spacing intervals wider as each row of the receiving trays is brought closer to said inspection area from said transport start end by the travel of said conveyor and, when said conveyor travels from said inspecting area to the end of transport, to cause the spacing intervals between the columns of said receiving trays to become narrower and to be equal to the column spacing intervals of a conveyor which is provided for a next process.

3. A device according to claim 1, wherein each of said receiving trays is provided with a loose fitting part which is formed at a lower front part of said tray in the direction of travel of said conveyor and is loosely fitted on the mounting bar located in front of said loose fitting part and with an inserting cutout part which is formed in the rear side face of said receiving tray and is arranged to engage with said mounting bar located in rear of said receiving tray; and said loose fitting part and said inserting cutout part are arranged in combination to effectively keep each of said receiving trays in a horizontal attitude while the conveyor is horizontally traveling.

4. A device according to claim 1, wherein each of said receiving trays is provided with an elastic receiving seat which is fitted into said receiving tray and has a through hole vertically formed in the center part thereof as a transmission light passage and also with a light blocking bottom face which is arranged on the bottom side of said tray to horizontally extend frontward and rearward from said hole; and by virtue of said light blocking bottom face, said light receiving means can be arranged closer to the lower side face of each of said receiving trays.

5. A device according to claim 2, wherein each of said receiving trays is provided with a loose fitting part which is formed at a lower front part of said tray in the direction of travel of said conveyor and is loosely fitted on the mounting bar located in front of said loose fitting part and with an inserting cutout part which is formed in the rear side face of said receiving tray and is arranged to engage with said mounting bar located in rear of said receiving tray; and said loose fitting part and said inserting cutout part are arranged in combination to effectively keep each of said receiving trays in a horizontal attitude while the conveyor is horizontally traveling.

6. A device according to claim 2, wherein each of said receiving trays is provided with an elastic receiving seat which is fitted into said receiving tray and has a through hole vertically formed in the center part thereof as a transmission light passage and also with a light blocking bottom face which is arranged on the bottom side of said tray to horizontally extend frontward and rearward from said hole; and by virtue of said light blocking bottom face, said light receiving means can be arranged closer to the lower side face of each of said receiving trays.

7. A device according to claim 3, wherein each of said receiving trays is provided with an elastic receiving seat which is fitted into said receiving tray and has a through hole vertically formed in the center part thereof as a transmission light passage and also with a light blocking bottom face which is arranged on the bottom side of said tray to horizontally extend frontward and rearward from said hole; and by virtue of said light blocking bottom face, said light receiving means can be arranged closer to the lower side face of each of said receiving trays.

8. A device according to claim 5, wherein each of said receiving trays is provided with an elastic receiving seat which is fitted into said receiving tray and has a through hole vertically formed in the center part thereof as a transmission light passage and also with a light blocking bottom face which is arranged on the bottom side of said tray to horizontally extend frontward and rearward from said hole; and by virtue of said light blocking bottom face, said light receiving means can be arranged closer to the lower side face of each of said receiving trays.

* * * * *